United States Patent
Leigh et al.

(10) Patent No.: US 9,821,155 B2
(45) Date of Patent: Nov. 21, 2017

(54) INDUCTIVE SIGNAL TRANSFER IN AN IMPLANTABLE MEDICAL DEVICE

(71) Applicant: Cochlear Limited, Macquarie University, NSW (AU)

(72) Inventors: Charles Roger Aaron Leigh, Macquarie Park (AU); Tony Burch, Macquarie Park (AU)

(73) Assignee: Cochlear Limited, Macquarie University, NSW (AU)

( * ) Notice: Subject to any disclaimer, the term of this patent is extended or adjusted under 35 U.S.C. 154(b) by 563 days.

(21) Appl. No.: 13/689,999

(22) Filed: Nov. 30, 2012

(65) Prior Publication Data

US 2014/0155685 A1    Jun. 5, 2014

(51) Int. Cl.
| | | |
|---|---|---|
| A61N 1/05 | (2006.01) | |
| A61N 1/375 | (2006.01) | |
| A61N 1/372 | (2006.01) | |
| A61N 1/36 | (2006.01) | |

(52) U.S. Cl.
CPC ........... *A61N 1/0541* (2013.01); *A61N 1/375* (2013.01); *A61N 1/37229* (2013.01); *A61N 1/36032* (2013.01)

(58) Field of Classification Search
CPC ............ A61N 1/36032; A61N 1/36125; A61N 1/372; A61N 1/37211; A61N 1/37229; A61N 1/37252; A61N 1/375; A61N 1/3787
See application file for complete search history.

(56) References Cited

U.S. PATENT DOCUMENTS

| | | | |
|---|---|---|---|
| 5,749,912 A | 5/1998 | Zhang et al. | |
| 6,308,101 B1 * | 10/2001 | Faltys | A61N 1/08 607/57 |
| 6,505,072 B1 * | 1/2003 | Linder et al. | 607/32 |
| 7,054,691 B1 | 5/2006 | Kuzma et al. | |
| 8,013,699 B2 | 9/2011 | Zimmerling | |
| 8,131,378 B2 | 3/2012 | Greenberg et al. | |
| 2006/0259096 A1 * | 11/2006 | Ayre et al. | 607/60 |

OTHER PUBLICATIONS

"Housing." Merriam-Webster.com. Merriam-Webster, n.d. Web. Aug. 24, 2015. <http://www.merriam-webster.com/dictionary/housing>.*

* cited by examiner

*Primary Examiner* — Charles A Marmor, II
*Assistant Examiner* — Carrie R Dorna
(74) *Attorney, Agent, or Firm* — Edell, Shapiro & Finnan, LLC

(57) ABSTRACT

An implantable medical device having a hermetically-sealed biocompatible housing configured to be implanted in a recipient. The implantable medical device includes at least one trans-housing transformer configured to transfer electrical signals through the housing.

20 Claims, 7 Drawing Sheets

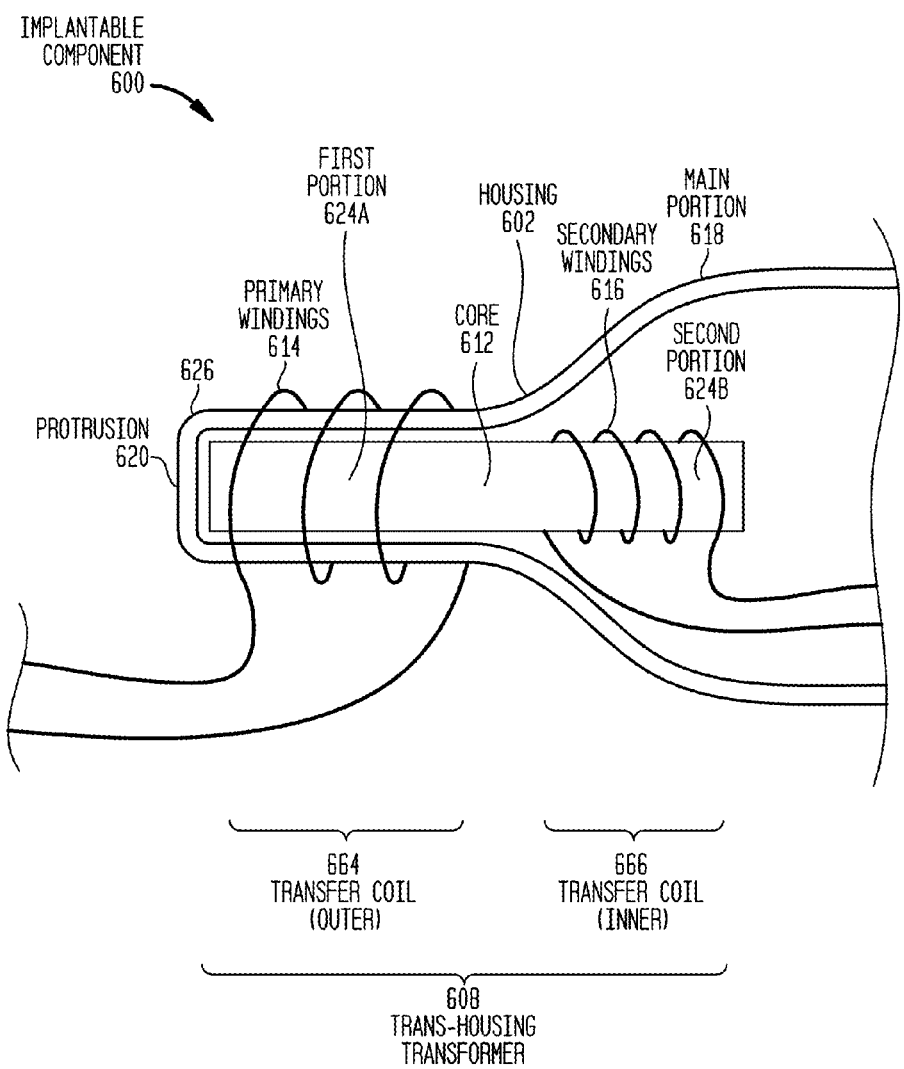

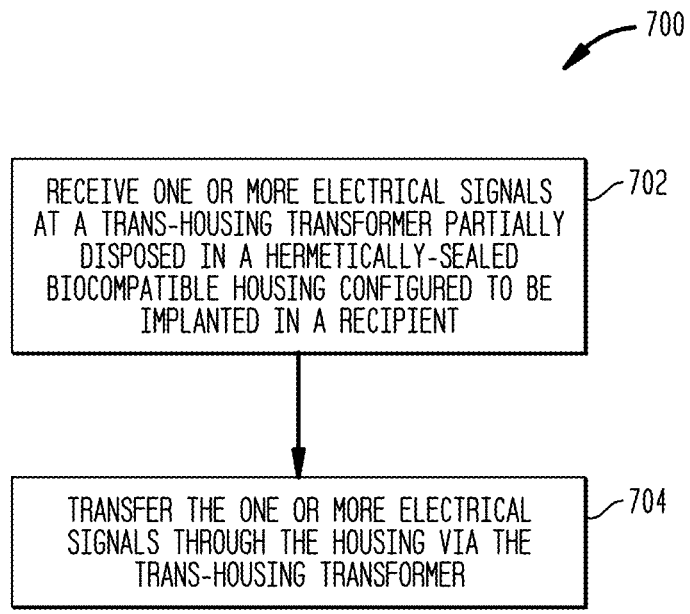

INDUCTIVE SIGNAL TRANSFER IN AN IMPLANTABLE MEDICAL DEVICE

BACKGROUND

Field of the Invention

The present invention relates generally to implantable medical devices, and more particularly, to inductive signal transfer in an implantable medical device.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process. Many of these functional components utilize power and/or data received from external components that are part of, or operate in conjunction with, the implantable medical device.

SUMMARY

In one aspect of the invention, an apparatus is provided. The apparatus comprises a hermetically-sealed biocompatible housing configured to be implanted in a recipient and at least one trans-housing transformer configured to transfer electrical signals through the housing.

In another aspect of the present invention, a method is provided. The method comprises receiving one or more electrical signals at a trans-housing transformer partially disposed in a hermetically-sealed biocompatible housing configured to be implanted in a recipient, and transferring, via the trans-housing transformer, the one or more electrical signals through the housing.

BRIEF DESCRIPTION OF THE DRAWINGS

Embodiments of the present invention are described herein in conjunction with the accompanying drawings, in which:

FIG. 6 is a partial cross-sectional view of a portion of an implantable medical device having a trans-housing transfer in accordance with embodiments of the present invention; and FIG. 7 is a flowchart of a method for using an implantable medical device having a trans-housing transfer in accordance with embodiments of the present invention.

DETAILED DESCRIPTION

Embodiments of the present invention are generally directed to an implantable medical device having a hermetically-sealed biocompatible housing configured to be implanted in a recipient. The implantable medical device also includes at least one trans-housing transformer configured to inductively transfer electrical signals through the housing.

Embodiments of the present invention are described herein primarily in connection with one type of implantable medical devices, namely hearing prostheses. Hearing prostheses include, but are not limited to, auditory brain stimulators, cochlear implants (also commonly referred to as cochlear implant devices, cochlear prostheses, and the like; simply "cochlear implants" herein), bone conduction devices, and mechanical stimulators. It is to be appreciated that embodiments of the present invention may be implemented in any implantable medical device now known or later developed.

Implantable medical devices generally include one or more electrical components positioned in a hermetic housing. There is also generally a need to transfer power to and/or from these electrical components and one or more components positioned outside (external to) the housing. Conventional arrangements achieve both of these objectives through the use of a hermetic feedthrough in the housing. More specifically, in conventional arrangements, electrical leads (wires) extend from the electrical components outside of the housing to the hermetic feedthrough. Additionally, electrical leads are disposed within the housing to connect the feedthrough to the electrical components. As such, conventional arrangements use a physical electrical connection, provided by a feedthrough that extends through the housing, to transfer signals to/from the electrical components outside of the housing to the electrical components within the housing.

Hermetic feedthroughs are one of the most complex mechanical structures in an implantable medical device and typically include an insulator (ceramic), one or more conductors (platinum), and one or more braze joints (TiCuNi or gold). Such feedthroughs are a significant source of device cost as well as device failure. Embodiments presented herein eliminate the use of a hermetic feedthrough to transfer signals between electrical components outside of an implantable housing and electrical components within the implantable housing. More specifically, embodiments presented herein use a trans-housing transformer to inductively transfer signals through a hermetic housing.

Figure 1:
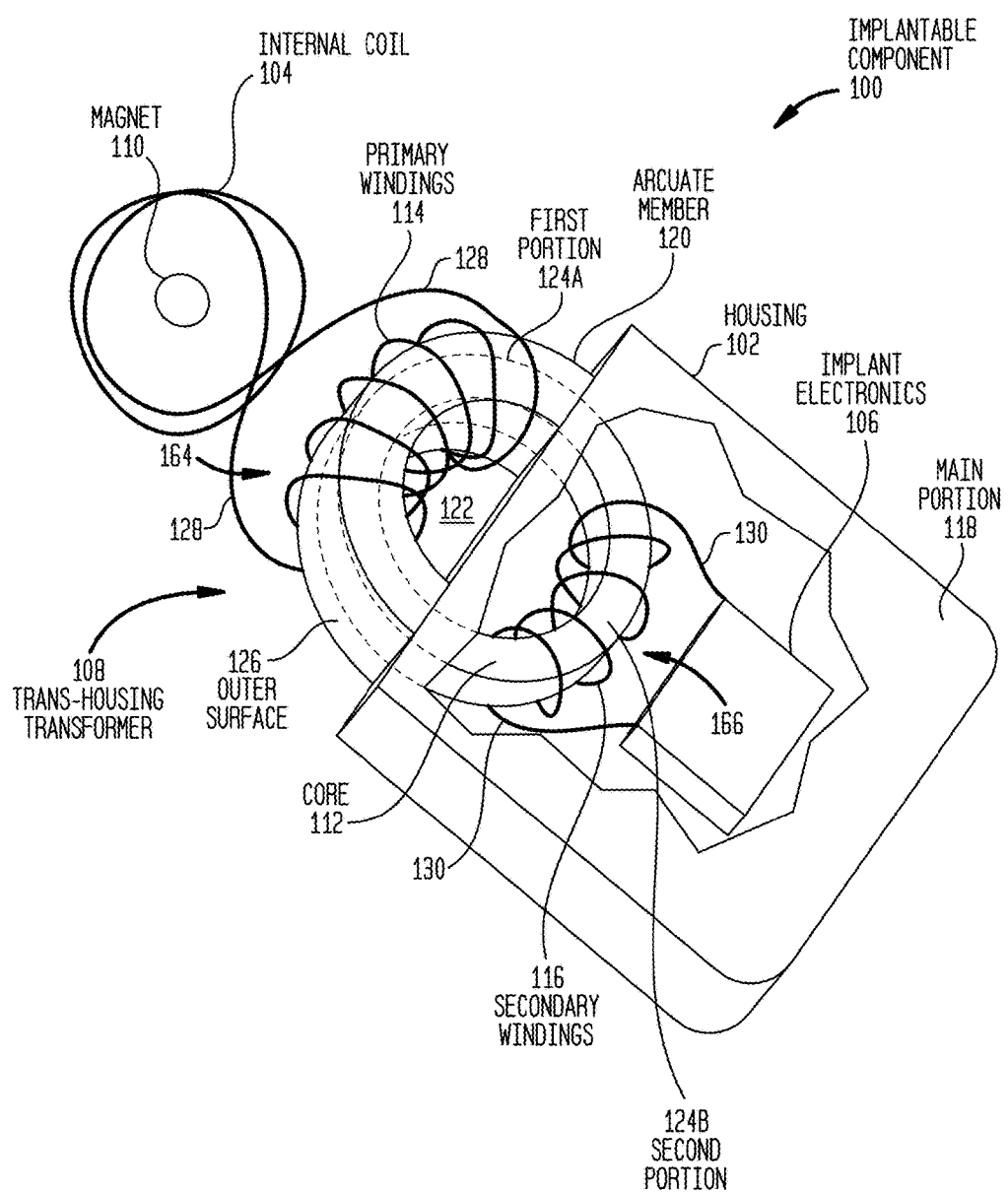
FIG. 1 is a perspective view of an implantable medical device having a trans-housing transformer in accordance with embodiments of the present invention.

FIG. 1 is a perspective view of an implantable component 100 of an exemplary hearing prosthesis in accordance with embodiments of the present invention, namely an active transcutaneous bone conduction device. The implantable component 100 is configured to be implanted underneath the skin of a recipient adjacent to the recipient's skull. Implantable component 100 comprises a housing 102 and an internal coil 104. The internal coil 104 is positioned outside (external to) housing 102 and is electrically coupled to implant electronics 106 within housing 102 via a trans-housing transformer 108. As used herein, a trans-housing transformer is a component that is configured to inductively transfer electrical signals through a hermetically-sealed housing without the use of a feedthrough or other direct electrical connection. The trans-housing transformer may comprise first and second inductively coupled coils disposed around a core. The first coil is disposed outside the hermetically-sealed housing, while the second coil is disposed inside the hermetically-sealed housing. The implant electronics 106 may include various electrical components of the implant (not shown for convenience). A portion of the housing 102 has been omitted from FIG. 1 to illustrate elements of trans-housing transformer 108 and the implant electronics 106.

In one embodiment, the internal coil 104 may be a two-turn electrically insulated platinum or gold wire antenna coil. A magnet 110 may be centrally located in internal coil 104 to assist in the alignment of an external coil (not shown in FIG. 1) with the internal coil 104 so that power and data may be transcutaneously transferred (possibly bi-directionally) between the external coil and the internal coil in the form of radio frequency (RF) signals. The magnet 110 may also assist in attachment of the external coil to the recipient.

The housing 102 is a hermetically sealed and biocompatible housing formed from, for example, titanium, platinum, ceramic, etc. Prior to implantation, the housing 102 and the internal coil 104 may be overmolded or coated with a silicone elastomer to create a uniform compliant surface suitable for implantation.

Trans-housing transformer 108 comprises a core 112 that is entirely positioned or disposed in the housing 102, a plurality of primary transformer windings 114 positioned external to the housing 102, and a plurality of secondary transformer windings 116 positioned within the housing 102. The plurality of primary windings 114 may be, for example, platinum or gold wire and collectively form an outer transfer coil 164 of the trans-housing transformer 108. The plurality of secondary windings 116 may be, for example, copper wire and collectively form an inner transfer coil 166 of the trans-housing transformer 108. Core 112 is a toroid core having an annular shape with a central aperture. In the embodiments of FIG. 1, toroid core 112 is a ferrite core. Alternatively, the toroid core 112 may be an iron core, a core formed from other magnetic materials, an air core, etc.

Housing 102 comprises a main compartment or portion 118 and an arcuate member 120 extending from the main portion 118. The arcuate member 120 defines an aperture 122 between the arcuate member and the main portion 118. A first portion 124A of the toroid core 112 is disposed in the arcuate member 120 and a second portion 124B of toroid core 112 is disposed in main portion 118. First portion 124A is shown in FIG. 1 using dashed lines, while, as noted above, a portion of housing 102 has been omitted from FIG. 1 to expose second portion 124B.

As shown in FIG. 1, the primary windings 114 are disposed around an outer surface 126 of the arcuate member 120 and, as such, around the first portion 124A of the toroid core 112. The secondary windings 116 are disposed around the second portion 124B of the toroid core 112 within the housing 102. As a result of the positioning of the primary windings 114 and the secondary windings 116 relative to toroid core 112, varying current in the primary windings creates a varying magnetic flux in the core and a corresponding varying current in the secondary windings. The varying current at the primary windings 114 is a result of RF signals (power and/or data) received at internal coil 104 that flows through wires 128 to primary windings 114. The varying magnetic flux in the core 112 induces current in the secondary windings 116 that are connected to the implant electronics 106 via the wires 130.

In the embodiments of FIG. 1, the positioning of toroid core 112 relative to the titanium housing 102 is such that there is minimal titanium across or perpendicular to the magnetic flux contained within the core. Additionally, the magnetic flux is mainly contained within the core 112 due to the much higher magnetic permeability (lower magnetic reluctivity) of the core (e.g., ferrite) compared to titanium or air. As such, the arrangement of FIG. 1 arrangement results in minimal eddy current losses during the inductive transfer of signals through the core 112.

FIG. 1 illustrates the use of only six (6) windings in each of the outer transfer coil 164 and the inner transfer coil 166. It is to be appreciated that different numbers of windings may be used in various embodiments of the present invention. It is also to be appreciated that the positioning of the windings in each of the outer transfer coil 164 and the inner transfer coil 166 of FIG. 1 is merely illustrative and that the positioning of the windings may vary in other embodiments. For example, in another embodiment, the secondary windings 116 may extend around both the first and second portions 124A, 124B of toroid core 112. That is, in certain embodiments the secondary windings 116 may be positioned around the entire circumference of the toroid core 112.

Figure 2:
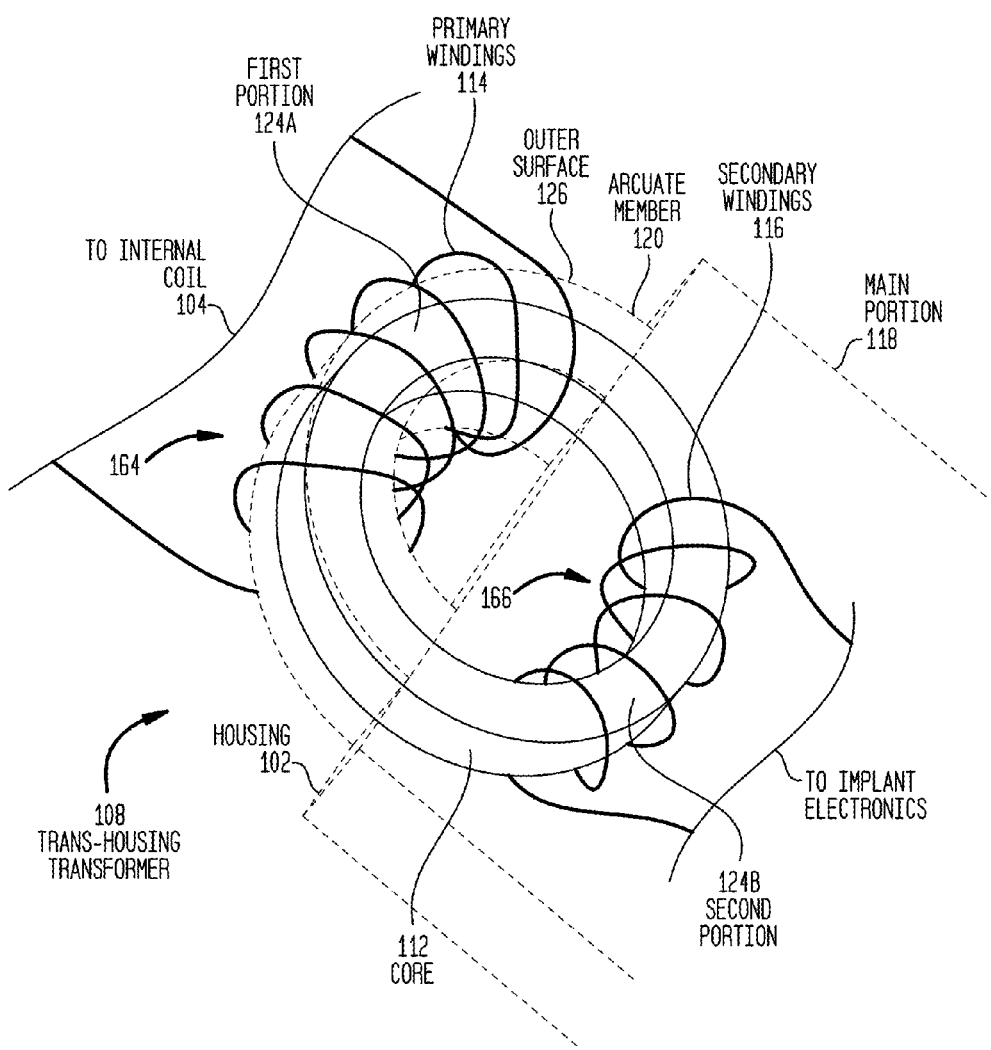
FIG. 2 is a perspective view of a trans-housing transformer in accordance with embodiments of the present invention.

FIG. 2 is an enlarged perspective view of trans-housing transformer 108 of FIG. 1. In FIG. 2, the housing 102 is shown using dashed lines in order to illustrate both portions 124A and 124B of the toroid core 112 and the secondary windings 116. As noted above, the first portion 124A of toroid core 112 is disposed within arcuate member 120 such that the outer surface 126 of arcuate member 120 is disposed between the toroid core 112 and the primary windings 114. That is, the primary windings 114 wrap around the outer surface 126 of the arcuate member 120.

In the embodiments of FIGS. 1 and 2, the toroid core 112 may have a size/shape so as to substantially fill arcuate member 120. However, it is to be appreciated that the toroid core 112 may have sizes, shapes, and or be formed from a magnetic material so as to optimize the transfer of signals from the internal coil 104 to the implant electronics 106.

As noted, in the embodiments of FIGS. 1 and 2, the housing 102 has a shape (main portion 118 and arcuate member 120) that provides an aperture 122 such that the primary windings 114 can wrap around a portion of the housing 102 and a first portion 124A of the toroid core 112, while the secondary windings 116 can wrap around a second portion 124B of the toroid core 112 within the housing 102. The exemplary shape of housing 102 in FIGS. 1 and 2 may be formed in a number of different ways. For example, in one embodiment the two symmetrical mating members (halves) (each including half of the main portion 118 and half of the arcuate member 120) may be formed and then welded together. Alternatively, the mating members may be asymmetrical to create a more accessible weld path. In another embodiment, a first member may form a majority of the main portion 118 and the arcuate member 120, but have an open top or side in which the internal components may be inserted. This open top/side may then be sealed by welding a substantially planar member across the open top/side (i.e., a body and a flat "cap" attached). In the above embodiments, the different parts of the housing may be formed using conventional fabrication techniques such as machining or pressing. Alternatively, techniques such as powder injection molding could also be employed.

FIGS. 1 and 2 have been primarily described with reference to the transfer of electrical signals from internal coil 104 to implant electronics 106 via trans-housing transformer 108. As such, the transfer coil 164 outside the housing 102 (closest to the internal coil 104) is considered to include primary windings, while the transfer coil 166 inside the housing 102 (closest to implant electronics 106) is considered to include secondary windings. It is to be appreciated that the trans-housing transformer 108 may transfer electrical signals in the opposite direction (i.e., from implant electronics 106 to internal coil 104) for transmission to an external component. As such, the use of "primary" and "secondary" to describe the windings is merely for purposes of illustration and should not be interpreted as implying a direction of signal transfer by the trans-housing transformer 108. Accordingly, in alternative embodiments where the direction of power transfer is opposite to that shown in FIGS. 1 and 2, the windings 116 may operate as "primary" windings and the windings 114 may operate as "secondary" windings.

Figure 3:
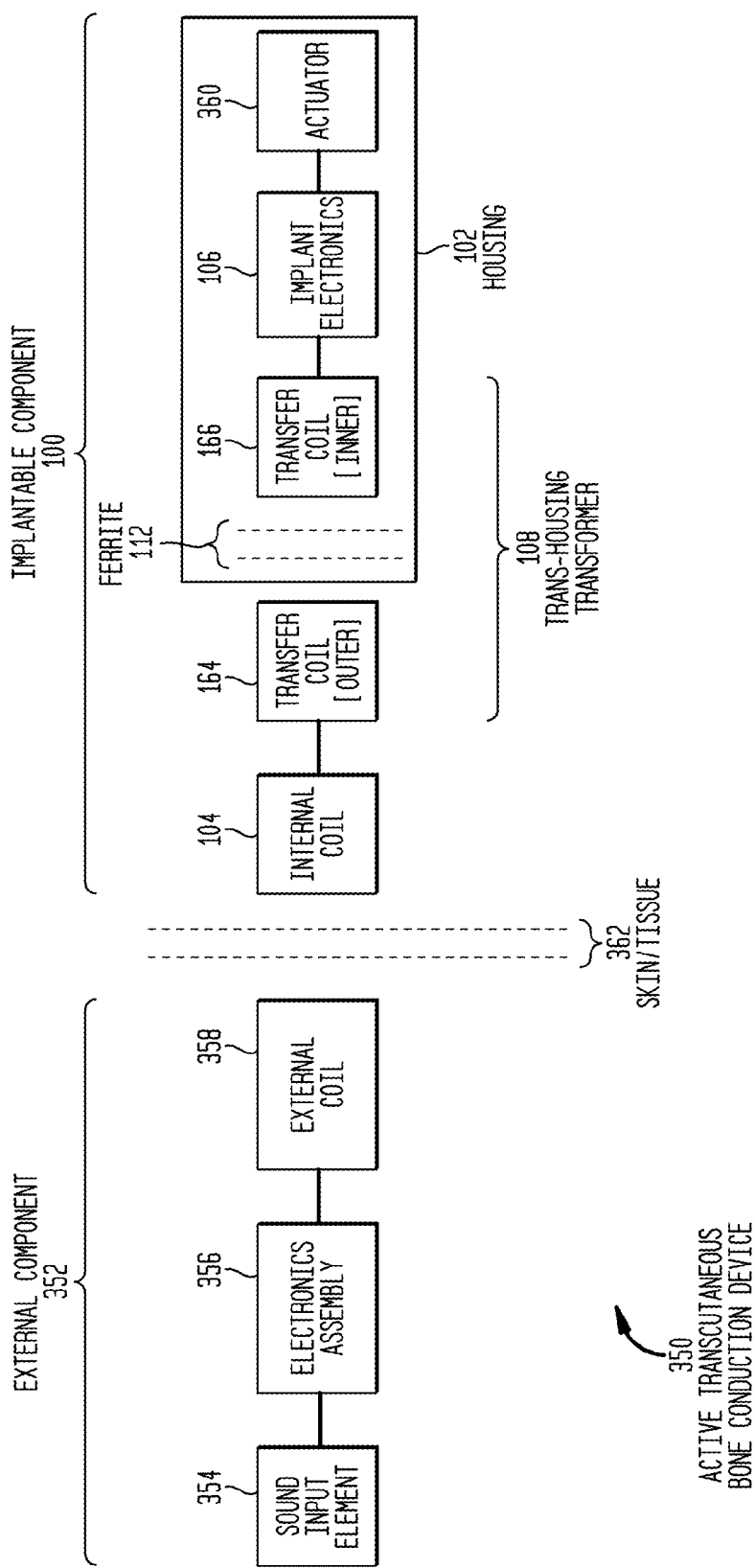
FIG. 3 is a functional block diagram of an active transcutaneous bone conduction device in accordance with embodiments of the present invention.

FIG. 3 is a block diagram schematically illustrating the implantable component 100 as part of an active transcutaneous bone conduction device 350. The active transcutaneous bone conduction device 350 includes implantable component 100 and an external component 352 configured to be worn by a recipient. As noted above, implantable component 100 comprises a hermetically-sealed housing 102, an internal coil 104, implant electronics 106, and a trans-housing transformer 108. External component 352 comprises a sound input element 354, an electronics assembly 356, and an external coil 358.

The sound input element 354 is configured to receive sound signals and may comprise, for example, a microphone, telecoil, etc. In an exemplary embodiment, the sound input element 354 may be located on or in the external component 352, on a cable or tube extending from the external component 352, etc. Alternatively, the sound input element 354 may be subcutaneously implanted in the recipient, or positioned in the recipient's ear. Sound input element 354 may also be a component that receives an electronic signal indicative of sound, such as, for example, from an external audio device. For example, sound input element 352 may receive a sound signal in the form of an electrical signal from an MP3 player electronically connected to the sound input element 354.

External component 352 also includes an electronics assembly 356 that comprises, for example, a sound processor (not shown) and/or various other operational components. In operation, sound input element 354 converts received sounds into electrical signals. These electrical signals are utilized by the sound processor and/or other components to generate electrical signals that are provided to external coil 358. The external coil 358 uses the electrical signals to generate RF signals that are transcutaneously transmitted through skin/tissue 362 of the recipient to internal coil 104 via a magnetic inductance link.

In the example of FIG. 3, trans-housing transformer 108 is provided to inductively transfer the signals received at the internal coil 104 through the housing 102 to implant electronics 106. The implant electronics 106 are electrically connected to inner transfer coil 166 and may comprise, for example, a signal generator or an implanted sound processor configured to use the signals received at the inner transfer coil 166 to generate electrical signals for delivery to a vibrating actuator/transducer 360. The actuator 360 is configured to convert the electrical signals into vibration for delivery to the recipient's cochlea via the skull. More specifically, the actuator 360 is mechanically coupled to the housing 102 and/or to the skull such that the vibration generated by the actuator 360 passes to the recipient's skull. In one embodiment, the housing 102 is substantially rigidly attached to a bone fixture (not shown) so that the vibration is transferred to the skull. The actuator 360 may be an electromagnetic (EM) actuator, piezoelectric actuator, etc.

FIGS. 1-3 primarily illustrate the use of a trans-housing transformer in an active transcutaneous bone conduction device. The trans-housing transformer eliminates the feedthrough used in conventional such devices to transfer signals from an internal coil to implant electronics in a hermetically sealed housing. In other words, use of the trans-housing transformer creates a feedthrough-free implant that, as a result, may have lower manufacturing costs and lower failure rates than devices that include a feedthrough.

In certain embodiments, a trans-housing transformer as presented herein may also be used to transfer power and/or data between implanted devices or modules. For example, a first module module may contain a battery and electronics, while a second module may include a functional component, such as an actuator. In such embodiments, the battery and electronics module may be electrically connected to the actuator module via a trans-housing transformer.

It is to be appreciated that other implantable medical devices, such as cochlear implants, mechanical stimulators, auditory brainstem implants (ABIs), deep brain stimulators, other functional electrical stimulation devices, etc. may also include an internal coil configured to receive power and/or data for electronics disposed in a hermetically sealed housing. Conventionally, such implantable medical devices also use a hermetic feedthrough to electrically connect the internal coil to the electronics within the hermetically sealed housing. It is to be appreciated that the trans-housing transformers presented herein may be used in such other implantable medical devices to eliminate the hermetic feedthrough connecting the internal coil to the electronics within the hermetically sealed housing.

Furthermore, certain implantable medical devices may also include one or more other functional mechanical or electrical components that are permanently or temporarily in a recipient (i.e., components to diagnose, prevent, monitor, treat or manage a disease, injury or symptom thereof, or to investigate, replace or modify of the recipient's anatomy or a physiological process). Each of these functional components generally has one or more electrical connections to the implant electronics within a hermetically-sealed housing. These electrical connections are generally used to provide control signals and/or power to the functional components or to receive data signals from the functional components. In conventional arrangements, these electrical connections also require use of hermetic feedthroughs (in additional to the internal coil feedthrough) to pass the electrical signals through the housing, thereby introducing additional sources of device cost and device failure. In accordance with embodiments of the present invention, one or more additional trans-housing transformers may be used to eliminate these functional component feedthroughs.

Figure 4:
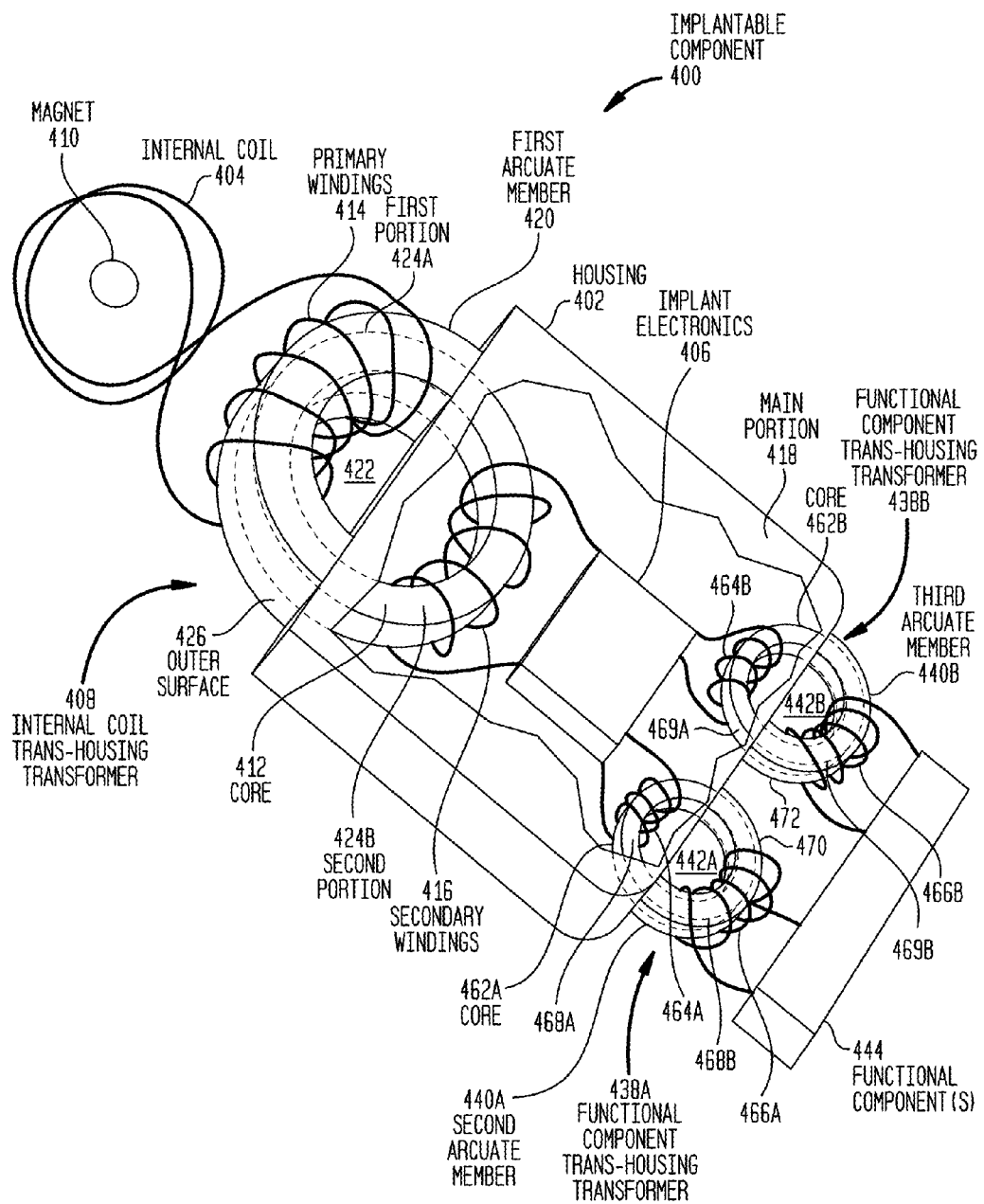
FIG. 4 is a perspective view of an implantable medical device having a plurality of trans-housing transformers in accordance with embodiments of the present invention.

FIG. 4 is a perspective view of an implantable component 400 of an exemplary implantable medical in accordance with embodiments of the present invention where trans-housing transformers are provided to replace an internal coil feedthrough and two functional component feedthroughs.

Implantable component 400 comprises a housing 402 and an internal coil 404 electrically coupled to implant electronics 406 within housing 402 via a first trans-housing transformer 408. A portion of housing 402 has been omitted from FIG. 4 to illustrate internal elements within housing 402 Implantable component 400 also comprises second and third trans-housing transformers 438A and 438B, respectively.

The internal coil 404 and first trans-housing transformer 408 are substantially similar to the internal coil 104 and trans-housing transformer 108, respectively, of FIG. 1. As such, in the example of FIG. 4, like reference numbers are used to indicate similarity to elements of FIG. 1. For completeness, a full description of internal coil 404 and first trans-housing transformer 408 is provided below.

The internal coil 404 forms an inductive link with an external coil (not shown) so that power and data may be transcutaneously transferred between the external and internal coils. A magnet 410 assists in the alignment of the external coil with the internal coil 404 and with attachment of the external coil to the recipient. The housing 402 comprises a main portion 418 and a first arcuate member 420 extending from the main portion 418 so as to define an aperture 422 between the arcuate member 420 and the main portion 418.

Trans-housing transformer 408 is sometimes referred to herein as an internal coil trans-housing transformer because it is configured to inductively transfer electrical signals from internal coil 404 to implant electronics 406. Internal coil trans-housing transformer 408 comprises a ferrite toroid core 412 that is entirely positioned or disposed in the housing 402, a plurality of primary windings 414 positioned external to the housing 402, and a plurality of secondary windings 416 positioned within the housing 402.

Similar to the arrangement of FIG. 1, a first portion 424A of the toroid core 412 is disposed in the arcuate member 420 and a second portion 424B of toroid core 412 is disposed in main portion 418. First portion 424A is shown in FIG. 4 using dashed lines, while, as noted above, a portion of housing 402 has been omitted from FIG. 4 to illustrate second portion 424B. Also similar to the arrangement of FIG. 1, the primary windings 414 are disposed around an outer surface 426 of the arcuate member 420 and, as such, around the first portion 424A of the toroid core 412 to form an outer transfer coil. The secondary windings 416 are disposed around the second portion 424B of the toroid core 412 within the housing 402 to form an inner transfer coil. As a result of the positioning of the primary windings 414 and the second windings 416 relative to toroid core 412, signals may be inductively transferred through housing 402 for delivery to implant electronics 406.

In the embodiments of FIG. 4, housing 402 also comprises a second arcuate member 440A extending from main portion 418 to define an aperture 442A between the second arcuate member 440A and the main portion 418, and a third arcuate member 440B extending from main portion 418 to define an aperture 442B between the third arcuate member 440B and the main portion 418.

Trans-housing transformers 438A and 438B are sometimes referred to herein as functional component trans-housing transformers because they are configured to inductively transfer electrical signals (potentially bi-directionally) between implant electronics 406 and functional component(s) 444. Functional component(s) 444 may comprise, for example, electrodes, a mechanical stimulator, sensors, etc.

Functional component trans-housing transformers 438A and 438B may comprise ferrite toroid cores 462A and 462B, respectively that are entirely positioned in the housing 402. Functional component trans-housing transformers 438A and 438B also comprise a plurality of primary windings 464A and 464B, respectively, positioned within the housing 402, and a plurality of secondary windings 466A and 466B, respectively, positioned external to the housing 402.

Toroid core 462A comprises a first portion 468A that is disposed in main portion 418, and a second portion 468B disposed in the second arcuate member 440A. Second portion 468B is shown in FIG. 4 using dashed lines, while, as noted above, a portion of housing 402 has been omitted from FIG. 4 to illustrate first portion 468A. The primary windings 464A are disposed around the first portion 468A of the toroid core 462A within the housing 402 to form an inner transfer coil. The secondary windings 466A are disposed around an outer surface 470 of the arcuate member 440A and, as such, around the second portion 468B of the toroid core 462A to form an outer transfer coil. As a result of the positioning of the primary windings 464A and the secondary windings 466A relative to toroid core 462A, signals from implant electronics 406 may be inductively transferred through housing 402 for delivery to functional component(s) 444.

Similarly, toroid core 462B comprises a first portion 469A that is disposed in main portion 418, and a second portion 469B disposed in the third arcuate member 440B. Second portion 469B is shown in FIG. 4 using dashed lines, while, as noted above, a portion of housing 402 has been omitted from FIG. 4 to expose first portion 469A. The primary windings 464B are disposed around the first portion 469A of the toroid core 462B within the housing 402 to form an inner transfer coil. The secondary windings 466B are disposed around an outer surface 472 of the arcuate member 440B and, as such, around the second portion 469B of the toroid core 462B to form an outer transfer coil. As a result of the positioning of the primary windings 464B and the secondary windings 466B relative to toroid core 462B, signals from implant electronics 406 may be inductively transferred through housing 402 for delivery to functional component(s) 444.

FIG. 4 has been primarily described with reference to the transfer of electrical signals from implant electronics 406 to functional component(s) 444. As such, the transfer coils within the housing 402 (closest to implant electronics 406) are referred to as including primary windings, while the transfer coils outside the housing 402 (closest to functional component(s) 444) are referred to as including secondary windings. It is to be appreciated that the functional component trans-housing transformers 438A and 438B may transfer electrical signals in the opposite direction (i.e., from functional component(s) 444 to implant electronics 406). As such, the use of "primary" and "secondary" to describe the windings is merely for purposes of illustration and should not be interpreted as implying a direction of signal transfer by the trans-housing transformers 438A and 438B.

Figure 5A:
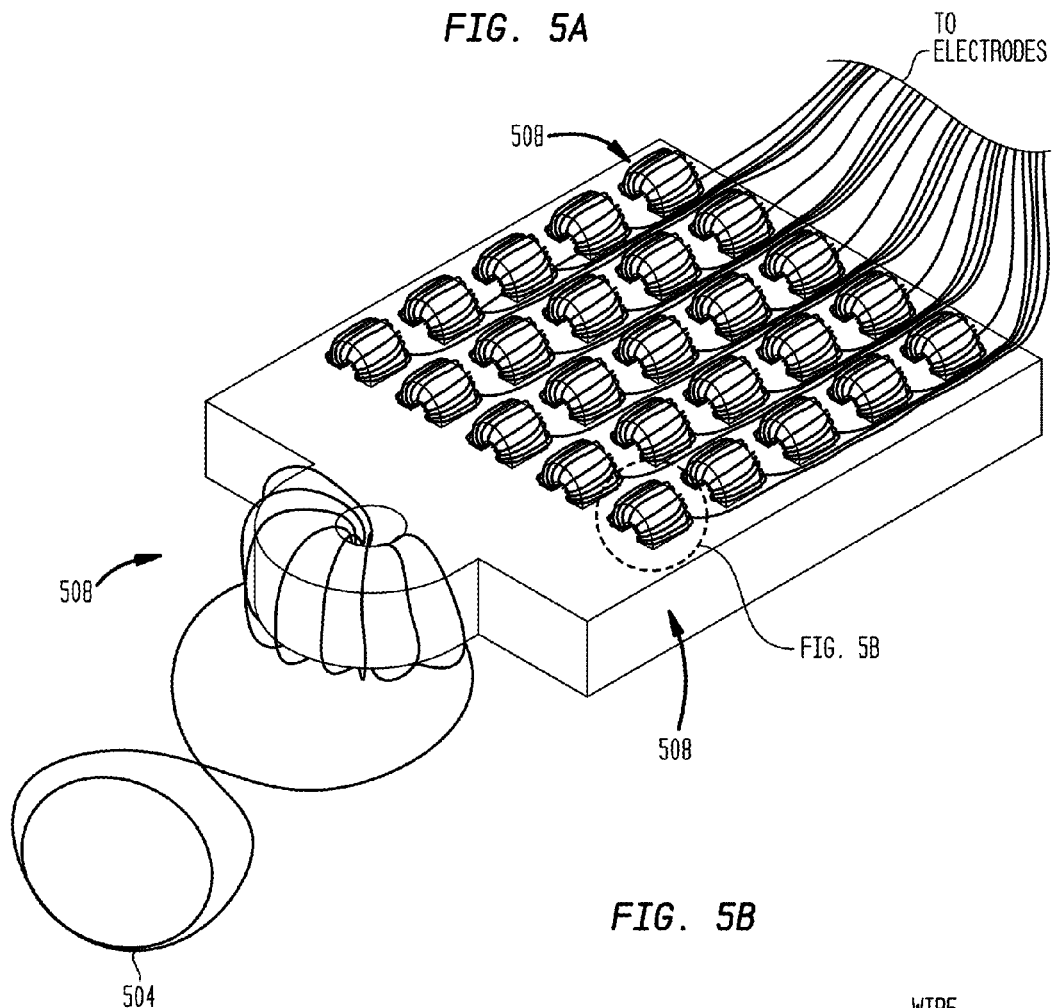
FIG. 5A is a perspective view of another implantable medical device having a plurality of trans-housing transformers in accordance with embodiments of the present invention.

It is to be appreciated that implantable components in accordance with embodiments presented herein may include any number of trans-housing transformers to transfer electrical signals to/from electronics within a hermetically sealed housing. For example, FIG. 5A illustrates an implantable component 500 of a cochlear implant that includes twenty-three trans-housing transformers 508. For ease of illustration, only several of the trans-housing transformers 508 are labeled in FIG. 5A.

In the specific embodiment of FIG. 5A, one of the trans-housing transformers 508 is an internal coil trans-housing transformer configured to transfer signals from an internal coil 504 to implant electronics (not shown) in a housing 502. The remaining twenty-two trans-housing transformers 508 are functional component trans-housing transformers configured to transfer electrical signals between the implant electronics in housing 502 and implanted electrodes (not shown) in an intra-cochlear electrode array (also not shown).

Figure 5B:
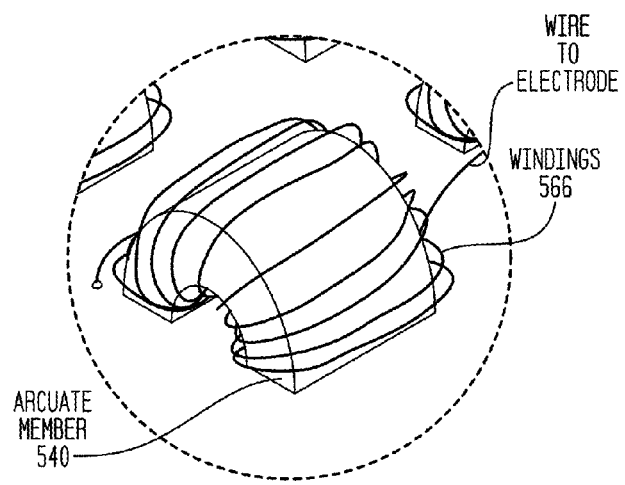
FIG. 5B is a perspective view of a portion of a trans-housing transformer of FIG. 5A.

FIG. 5B is an enlarged view of a portion of a trans-housing transformer 508 of FIG. 5A illustrating a plurality of windings 566 wrapped around an arcuate member 540 that includes a portion of a toroid core (not shown).

FIGS. 1-5B, above, illustrate embodiments of the present invention where the core of the trans-housing transformer is a ferrite toroid core. It is to be appreciated that other cores may be used in alternative embodiments of the present invention. In particular, FIG. 6 illustrates an alternative embodiment of the present invention in which a cylindrical linear core is used in place of the toroid core.

FIG. 6 is a side view of a portion of an implantable component 600 having a trans-housing transformer 608 to transfer signals through a hermetically sealed housing 602. For ease of illustration, housing 602 is shown in cross-section to illustrate the elements positioned within the housing.

In the embodiments of FIG. 6, the housing 602 comprises a main portion 618 and a protrusion 620. Trans-housing transformer 608 comprises an elongate core 612 that is entirely positioned or disposed in the housing 602, a plurality of primary windings 614 positioned external to the housing 602, and a plurality of secondary windings 616 positioned within the housing 602. More specifically, a first portion 624A of the elongate core 612 is disposed in the protrusion 620 and a second portion 624B of elongate core 612 is disposed in main portion 618.

As shown, the primary windings 614 are disposed around an outer surface 626 of the protrusion 620 and, as such, around the first portion 624A of the elongate core 612 to form an outer transfer coil 664. The secondary windings 616 are disposed around the second portion 624B of the elongate core 612 within the housing 602 to form an inner transfer coil 666. As a result of the positioning of the primary windings 614 and the second windings 616 relative to elongate core 612, varying current in the primary windings creates a varying magnetic flux in the core and a corresponding varying magnetic field through the secondary windings. In one embodiment, the varying current at the primary windings 614 is a result of RF signals (power and/or data) received at an internal coil (not shown) and the current flows through one or more wires to primary windings 614. The varying magnetic field through the secondary windings 616 generates current that is carried by one or more wires to implant electronics (not shown) in housing 602.

FIG. 7 is a flowchart of a method 700 for using an implantable medical device having a trans-housing transfer in accordance with embodiments of the present invention. Method 700 begins at step 702 where one or more electrical signals are received at a trans-housing transformer partially disposed in a hermetically-sealed biocompatible housing configured to be implanted in a recipient. At step 704, the one or more electrical signals are transferred through the housing via the trans-housing transformer.

In accordance with one embodiment of FIG. 7, the trans-housing transformer comprises a core entirely disposed in the housing that has first and second portions. In such embodiments, a plurality of secondary windings may be positioned within the housing and disposed around the second portion of the magnetic core, while a plurality of primary windings may be positioned external to the housing and disposed around the first portion of the magnetic core. In such embodiments, the one or more electrical signals are received at the primary windings to induce a varying current in the primary windings that creates a varying magnetic flux in the core and a corresponding varying magnetic field through the secondary windings.

In accordance with another embodiment of FIG. 7, the one or more electrical signals are received at an internal coil configured to be implanted in the recipient. The one or more electrical signals are then provided to the trans-housing transformer (minus any losses resulting from resistance, inductance or other well-known electrical phenomenon) where the one or more electrical signals are transferred through the housing to implant electronics positioned in the housing.

Embodiments of the present invention have been primarily described with reference to toroid and elongate cores. It is to be appreciated that alternative embodiments of the present invention may use different shaped or sized cores than those described above. For example alternative cores may be oval, square, rectangular, etc. In general, the shape of the core should be such that the core forms a continuous path for magnetic flux to follow and that wires can be wrapped around it in a location exterior to the hermetic enclosure and a location interior to the enclosure. Housings in accordance with embodiments of the present invention may have different shapes than those described above to accommodate such different core shapes (i.e., the arcuate member or protrusion may be replaced with a member best suited for use with the selected core shape). Additionally, the arcuate members, protrusions, or other shapes to accommodate a portion of a core may be disposed at any of a number of different locations within a housing (i.e., top, bottom, sides, etc.).

Embodiments of the present invention have also been primarily described with reference to ferrite cores. It is to be appreciated that alternative embodiments of the present invention may use different types of cores (e.g., different magnetic materials, air, etc.) appropriate for the transfer of the subject electrical signals. More specifically, signals to be transferred in different implantable medical devices or in different parts of an implantable medical device may have different spectral energies. Different core materials or core shapes may be better suited to transfer signals at the different spectral energies and, as such, the selection of a core material may depend on the spectral energy of the signals that are to be transferred through that core. In certain embodiments, different types of cores may be used within the same implantable medical device (i.e., one type of core for an internal coil trans-housing transformer and one type of core for a functional component trans-housing transformer).

While various embodiments of the present invention have been described above, it should be understood that they have been presented by way of example only, and not limitation. It will be apparent to persons skilled in the relevant art that various changes in form and detail can be made therein without departing from the spirit and scope of the invention.

Thus, the breadth and scope of the present invention should not be limited by any of the above-described exemplary embodiments, but should be defined only in accordance with the following claims and their equivalents.

All documents, patents, journal articles and other materials cited in the present application are hereby incorporated by reference.

What is claimed is:

1. An apparatus comprising:
a hermetically-sealed biocompatible unitary housing configured to be implanted in a recipient;
implant electronics positioned in the housing;
at least one trans-housing transformer configured to transfer electrical signals through the housing, wherein the at least one trans-housing transformer comprises:
a core entirely positioned in the housing and having first and second portions;
a plurality of secondary windings positioned within the housing and connected to the implant electronics, wherein the plurality of secondary windings are disposed around the second portion of the core; and
a plurality of primary windings positioned external to the housing and disposed around the first portion of the core such that varying current in the primary windings creates a varying magnetic flux in the core and a corresponding varying magnetic field through the secondary windings.

2. The apparatus of claim 1, wherein the core comprises a ferrite toroid core and wherein the housing comprises a main portion and an arcuate member extending from the main portion so as to define an aperture between the arcuate member and the main portion, wherein a first portion of the toroid core is disposed in the arcuate member such that the primary windings are disposed around an outer surface of the arcuate member so as to extend through the aperture and the secondary windings are disposed around a second portion of the toroid within the housing.

3. The apparatus of claim 1, wherein the core comprises an elongate ferrite core and wherein the housing comprises a main portion and a protrusion extending from the main portion, wherein the protrusion is configured to receive a first portion of the elongate core such that the primary windings are disposed around an outer surface of the protrusion and the secondary windings are disposed around a second portion of the elongate core within the housing.

4. The apparatus of claim 1, further comprising:
an implantable internal coil positioned external to the housing and electrically connected to the primary windings of the at least one trans-housing transformer positioned external to the housing, wherein the implantable internal coil is configured to receive electrical signals transmitted by one or more devices positioned external to the recipient, and
wherein the at least one trans-housing transformer is configured to transfer electrical signals received by the internal coil to the implant electronics positioned in the housing.

5. The apparatus of claim 4, wherein the at least one trans-housing transformer comprises first and second trans-housing transformers, wherein the internal coil is electrically connected to the first trans-housing transformer and wherein the apparatus further comprises:
at least one functional component positioned external to the housing, and
wherein a portion of the second trans-housing transformer is electrically connected to the at least one functional component and is configured to transfer electrical signals generated by the implant electronics disposed in the housing to the at least one functional component.

6. The apparatus of claim 1, wherein the at least one trans-housing transformer comprises a plurality of trans-housing transformers configured to independently transfer separate electrical signals through the housing.

7. The apparatus of claim 1, further comprising:
at least one functional component positioned external to the housing; and the implant electronics disposed within the housing and configured to generate electrical signals for use by the at least one functional component,
wherein the at least one trans-housing transformer is configured to transfer the electrical signals generated by the implant electronics to the at least one functional component.

8. The apparatus of claim 7, wherein the at least one functional component is a component configured to at least one of electrically or mechanically stimulate the recipient.

9. The apparatus of claim 1, wherein the housing comprises a titanium housing and the core comprises a ferrite core.

10. An implantable medical device comprising:
an external coil configured to be worn by a recipient;
a hermetically-sealed biocompatible unitary housing configured to be implanted in a recipient;
implant electronics positioned in the housing;
an implantable internal coil positioned external to the housing and configured to receive electrical signals transmitted by the external coil; and
at least one trans-housing transformer having a first portion positioned outside of the housing and connected to the internal coil and a second portion positioned inside of the housing and connected to the implant electronics and configured to transfer the electrical signals received at the internal coil through the housing to the implant electronics, wherein the at least one trans-housing transformer comprises:
a core entirely positioned in the housing and having first and second portions;
a plurality of secondary windings forming the second portion of the at least one trans-housing transformer and disposed around the second portion of the core; and
a plurality of primary windings forming the first portion of the at least one trans-housing transformer and disposed around the first portion of the core such that varying current in the primary windings creates a varying magnetic flux in the core and a corresponding varying magnetic field through the secondary windings.

11. The implantable medical device of claim 10, wherein the core comprises a ferrite toroid core and wherein the housing comprises a main portion and an arcuate member extending from the main portion to define an aperture between the arcuate member and the main portion, wherein a first portion of the toroid core is disposed in the arcuate member such that the primary windings are disposed around an outer surface of the arcuate member so as to extend through the aperture and the secondary windings are disposed around a second portion of the toroid within the housing.

12. The implantable medical device of claim 10, wherein the core comprises an elongate ferrite core and wherein the housing comprises a main portion and a protrusion extending from the main portion, wherein the protrusion is configured to receive a first portion of the elongate core such that the primary windings are disposed around an outer surface of the protrusion and the secondary windings are disposed around a second portion of the elongate core within the housing.

13. The implantable medical device of claim 10, wherein the at least one trans-housing transformer comprises first and second trans-housing transformers, wherein the internal coil is electrically connected to the first trans-housing transformer and wherein the apparatus further comprises:
at least one functional component positioned external to the housing, and
wherein a portion of the second trans-housing transformer is electrically connected to the at least one functional component and is configured to transfer electrical signals generated by the implant electronics disposed in the housing to the at least one functional component.

14. The implantable medical device of claim 13, wherein the at least one functional component is a component configured to at least one of electrically or mechanically stimulate the recipient.

15. An implantable hearing prosthesis, comprising:
a hermetically-sealed biocompatible unitary housing configured to be implanted in a recipient, wherein the housing comprises a main portion and a protrusion extending from the main portion,
implant electronics positioned in the housing;
at least one trans-housing transformer configured to transfer electrical signals through the housing, comprising:
an elongate core positioned entirely within the housing, wherein a first portion of the elongate core is disposed in the protrusion and a second portion of the elongate core is positioned within the main portion,
a plurality of secondary windings positioned within the housing around the second portion of the elongate core, and
a plurality of primary windings positioned external to the housing disposed around the protrusion and the first portion of the core such that varying current in the primary windings creates a varying magnetic flux in the core and a corresponding varying magnetic field through the secondary windings;
an implantable internal coil positioned external to the housing and electrically connected to the plurality of primary windings positioned external to the housing and configured to receive transcutaneous electrical signals transmitted by one or more devices positioned external to the recipient,
wherein the trans-housing transformer is configured to transfer electrical signals received by the internal coil to the implant electronics positioned in the housing.

16. The implantable hearing prosthesis of claim 15, wherein the housing comprises a titanium housing and the core comprises a ferrite core.

17. The implantable hearing prosthesis of claim 15, wherein the at least one trans-housing transformer comprises first and second trans-housing transformers, wherein the internal coil is electrically connected to the first trans-housing transformer and wherein the implantable hearing prosthesis further comprises:
at least one functional component positioned external to the housing, and
wherein a portion of the second trans-housing transformer is electrically connected to the at least one functional component and is configured to transfer electrical signals generated by the implant electronics disposed in the housing to the at least one functional component.

18. The implantable hearing prosthesis of claim 15, wherein the at least one trans-housing transformer comprises a plurality of trans-housing transformers configured to independently transfer separate electrical signals through the housing.

19. The implantable hearing prosthesis of claim 18, further comprising:
at least one functional component positioned external to the housing; and the implant
electronics disposed within the housing and configured to generate electrical signals for use by the at least one functional component,
wherein the at least one of the plurality of trans-housing transformers is configured to transfer the electrical signals generated by the implant electronics to the at least one functional component.

20. The implantable hearing prosthesis of claim 19, wherein the at least one functional component is a component configured to at least one of electrically or mechanically stimulate the recipient.

* * * * *